(12) United States Patent
Tokarz et al.

(10) Patent No.: US 11,844,549 B2
(45) Date of Patent: Dec. 19, 2023

(54) SURGICAL ACCESS DEVICE INCLUDING A UNIVERSAL FLUID FLOW VALVE

(71) Applicant: Covidien LP, Mansfield, MA (US)

(72) Inventors: Christopher A Tokarz, Torrington, CT (US); Douglas M. Pattison, East Hartford, CT (US); Kevin Desjardin, Prospect, CT (US); Astley C. Lobo, West Haven, CT (US)

(73) Assignee: Covidien LP, Mansfield, MA (US)

( * ) Notice: Subject to any disclaimer, the term of this patent is extended or adjusted under 35 U.S.C. 154(b) by 490 days.

(21) Appl. No.: 17/071,134

(22) Filed: Oct. 15, 2020

(65) Prior Publication Data

US 2022/0117630 A1    Apr. 21, 2022

(51) Int. Cl.
*A61B 17/34* (2006.01)

(52) U.S. Cl.
CPC ...... *A61B 17/3498* (2013.01); *A61B 17/3423* (2013.01); *A61B 2017/3425* (2013.01); *A61B 2017/3486* (2013.01)

(58) Field of Classification Search
CPC ............ A61B 17/3498; A61B 17/3423; A61B 17/3462; A61B 17/3474; A61B 2017/3486; A61M 39/223–2039/224; A61M 29/00–02; A61M 25/10185; A61M 25/10186; A61M 13/00–006; A61M 2039/229
See application file for complete search history.

(56) References Cited

U.S. PATENT DOCUMENTS

| 397,060 A | 1/1889 | Knapp |
| 512,456 A | 1/1894 | Sadikova |
| 1,213,005 A | 1/1917 | Pillsbury |
| 2,912,981 A | 11/1959 | Keough |
| 2,936,760 A | 5/1960 | Gains |
| 3,039,468 A | 6/1962 | Price |
| 3,050,066 A | 8/1962 | Koehn |
| 3,253,594 A | 5/1966 | Matthews et al. |

(Continued)

FOREIGN PATENT DOCUMENTS

| EP | 0480653 A1 | 4/1992 |
| EP | 0610099 A2 | 8/1994 |

(Continued)

*Primary Examiner* — Darwin P Erezo
*Assistant Examiner* — Brigid K Byrd
(74) *Attorney, Agent, or Firm* — Carter, DeLuca & Farrell LLP (57) ABSTRACT

A surgical access device includes a cannula, an instrument housing coupled to the cannula, a port coupled to the instrument housing, and a valve disposed within the port. The cannula includes an elongated shaft defining an access lumen and an inflation lumen therethrough. The port includes an inflation channel and an insufflation channel defined therethrough. The inflation channel is in fluid communication with the inflation lumen of the cannula and the insufflation channel is in fluid communication with the access lumen of the cannula. The valve is movable within the port between an inflation position in which a passageway defined through the valve is aligned with the inflation channel of the port, and an insufflation position in which the passageway of the valve is aligned with the insufflation channel of the port.

20 Claims, 6 Drawing Sheets

(56) References Cited

U.S. PATENT DOCUMENTS

| | | |
|---|---|---|
| 3,397,699 A | 8/1968 | Kohl |
| 3,545,443 A | 12/1970 | Ansari et al. |
| 3,713,447 A | 1/1973 | Adair |
| 3,774,596 A | 11/1973 | Cook |
| 3,800,788 A | 4/1974 | White |
| 3,882,852 A | 5/1975 | Sinnreich |
| 3,896,816 A | 7/1975 | Mattler |
| 3,961,632 A | 6/1976 | Moossun |
| RE29,207 E | 5/1977 | Bolduc et al. |
| 4,083,369 A | 4/1978 | Sinnreich |
| 4,217,889 A | 8/1980 | Radovan et al. |
| 4,243,050 A | 1/1981 | Littleford |
| 4,276,874 A | 7/1981 | Wolvek et al. |
| 4,312,353 A | 1/1982 | Shahbabian |
| 4,327,709 A | 5/1982 | Hanson et al. |
| 4,345,606 A | 8/1982 | Littleford |
| 4,411,654 A | 10/1983 | Boarini et al. |
| 4,416,267 A | 11/1983 | Garren et al. |
| 4,490,137 A | 12/1984 | Moukheibir |
| 4,496,345 A | 1/1985 | Hasson |
| 4,574,806 A | 3/1986 | McCarthy |
| 4,581,025 A | 4/1986 | Timmermans |
| 4,596,554 A | 6/1986 | Dastgeer |
| 4,596,559 A | 6/1986 | Teischhacker |
| 4,608,965 A | 9/1986 | Anspach, Jr. et al. |
| 4,644,936 A | 2/1987 | Schiff |
| 4,654,030 A | 3/1987 | Moll et al. |
| 4,685,447 A | 8/1987 | Iversen et al. |
| 4,701,163 A | 10/1987 | Parks |
| 4,738,666 A | 4/1988 | Fuqua |
| 4,769,038 A | 9/1988 | Bendavid et al. |
| 4,772,266 A | 9/1988 | Groshong |
| 4,779,611 A | 10/1988 | Grooters et al. |
| 4,784,133 A | 11/1988 | Mackin |
| 4,793,348 A | 12/1988 | Palmaz |
| 4,798,205 A | 1/1989 | Bonomo et al. |
| 4,800,901 A | 1/1989 | Rosenberg |
| 4,802,479 A | 2/1989 | Haber et al. |
| 4,813,429 A | 3/1989 | Eshel et al. |
| 4,840,613 A | 6/1989 | Balbierz |
| 4,854,316 A | 8/1989 | Davis |
| 4,861,334 A | 8/1989 | Nawaz |
| 4,865,593 A | 9/1989 | Ogawa et al. |
| 4,869,717 A | 9/1989 | Adair |
| 4,888,000 A | 12/1989 | McQuilkin et al. |
| 4,899,747 A | 2/1990 | Garren et al. |
| 4,917,668 A | 4/1990 | Haindl |
| 4,931,042 A | 6/1990 | Holmes et al. |
| 4,955,895 A | 9/1990 | Sugiyama et al. |
| 5,002,557 A | 3/1991 | Hasson |
| 5,009,643 A | 4/1991 | Reich et al. |
| 5,030,206 A | 7/1991 | Lander |
| 5,030,227 A | 7/1991 | Rosenbluth et al. |
| 5,074,871 A | 12/1991 | Groshong |
| 5,098,392 A | 3/1992 | Fleischhacker et al. |
| 5,104,383 A | 4/1992 | Shichman |
| 5,116,318 A | 5/1992 | Hillstead |
| 5,116,357 A | 5/1992 | Eberbach |
| 5,122,122 A | 6/1992 | Allgood |
| 5,122,155 A | 6/1992 | Eberbach |
| 5,137,512 A | 8/1992 | Burns et al. |
| 5,141,494 A | 8/1992 | Danforth et al. |
| 5,141,515 A | 8/1992 | Eberbach |
| 5,147,302 A | 9/1992 | Euteneuer et al. |
| 5,147,316 A | 9/1992 | Castillenti |
| 5,147,374 A | 9/1992 | Fernandez |
| 5,158,545 A | 10/1992 | Trudell et al. |
| 5,159,925 A | 11/1992 | Neuwirth et al. |
| 5,163,949 A | 11/1992 | Bonutti |
| 5,176,692 A | 1/1993 | Wilk et al. |
| 5,176,697 A | 1/1993 | Hasson et al. |
| 5,183,463 A | 2/1993 | Debbas |
| 5,188,596 A | 2/1993 | Condon et al. |
| 5,188,630 A | 2/1993 | Christoudias |
| 5,195,507 A | 3/1993 | Bilweis |
| 5,201,742 A | 4/1993 | Hasson |
| 5,201,754 A | 4/1993 | Crittenden et al. |
| 5,209,725 A | 5/1993 | Roth |
| 5,215,526 A | 6/1993 | Deniega et al. |
| 5,222,970 A | 6/1993 | Reeves |
| 5,226,890 A | 7/1993 | Ianniruberto et al. |
| 5,232,446 A | 8/1993 | Arney |
| 5,232,451 A | 8/1993 | Freitas et al. |
| 5,234,454 A | 8/1993 | Bangs |
| 5,250,025 A | 10/1993 | Sosnowski et al. |
| 5,258,026 A | 11/1993 | Johnson et al. |
| 5,269,753 A | 12/1993 | Wilk |
| 5,290,249 A | 3/1994 | Foster et al. |
| 5,308,327 A | 5/1994 | Heaven et al. |
| 5,309,896 A | 5/1994 | Moll et al. |
| 5,314,443 A | 5/1994 | Rudnick |
| 5,318,012 A | 6/1994 | Wilk |
| 5,330,497 A | 7/1994 | Freitas et al. |
| 5,342,307 A | 8/1994 | Euteneuer et al. |
| 5,346,504 A | 9/1994 | Ortiz et al. |
| 5,359,995 A | 11/1994 | Sewell, Jr. |
| 5,361,752 A | 11/1994 | Moll et al. |
| 5,370,134 A | 12/1994 | Chin et al. |
| 5,383,889 A | 1/1995 | Warner et al. |
| 5,397,311 A | 3/1995 | Walker et al. |
| 5,402,772 A | 4/1995 | Moll et al. |
| 5,407,433 A | 4/1995 | Loomas |
| 5,431,173 A | 7/1995 | Chin et al. |
| 5,445,615 A | 8/1995 | Yoon |
| 5,468,248 A | 11/1995 | Chin et al. |
| 5,514,091 A | 5/1996 | Yoon |
| 5,514,153 A | 5/1996 | Bonutti |
| 5,540,658 A | 7/1996 | Evans et al. |
| 5,540,711 A | 7/1996 | Kieturakis et al. |
| 5,607,441 A | 3/1997 | Sierocuk et al. |
| 5,607,443 A | 3/1997 | Kieturakis et al. |
| 5,632,761 A | 5/1997 | Smith et al. |
| 5,656,013 A | 8/1997 | Yoon |
| 5,667,479 A | 9/1997 | Kieturakis |
| 5,667,520 A | 9/1997 | Bonutti |
| 5,704,372 A | 1/1998 | Moll et al. |
| 5,707,382 A | 1/1998 | Sierocuk et al. |
| 5,713,869 A | 2/1998 | Morejon |
| 5,722,986 A | 3/1998 | Smith et al. |
| 5,728,119 A | 3/1998 | Smith et al. |
| 5,730,748 A | 3/1998 | Fogarty et al. |
| 5,730,756 A | 3/1998 | Kieturakis et al. |
| 5,738,628 A | 4/1998 | Sierocuk et al. |
| 5,755,693 A | 5/1998 | Walker et al. |
| 5,762,604 A | 6/1998 | Kieturakis |
| 5,772,680 A | 6/1998 | Kieturakis et al. |
| 5,779,728 A | 7/1998 | Lunsford et al. |
| 5,797,947 A | 8/1998 | Mollenauer |
| 5,803,901 A | 9/1998 | Chin et al. |
| 5,810,867 A | 9/1998 | Zarbatany et al. |
| 5,814,060 A | 9/1998 | Fogarty et al. |
| 5,836,913 A | 11/1998 | Orth et al. |
| 5,836,961 A | 11/1998 | Kieturakis et al. |
| 5,865,802 A | 2/1999 | Yoon et al. |
| 5,865,812 A * | 2/1999 | Correia .............. A61B 17/3498 604/167.01 |
| 5,893,866 A | 4/1999 | Hermann et al. |
| 5,925,058 A | 7/1999 | Smith et al. |
| 6,099,511 A * | 8/2000 | Devos ................ A61M 5/1408 604/82 |
| 6,361,543 B1 | 3/2002 | Chin et al. |
| 6,368,337 B1 | 4/2002 | Kieturakis et al. |
| 6,375,665 B1 | 4/2002 | Nash et al. |
| 6,379,372 B1 | 4/2002 | Dehdashtian et al. |
| 6,432,121 B1 | 8/2002 | Jervis |
| 6,447,529 B2 | 9/2002 | Fogarty et al. |
| 6,468,205 B1 | 10/2002 | Mollenauer et al. |
| 6,506,200 B1 | 1/2003 | Chin |
| 6,514,272 B1 | 2/2003 | Kieturakis et al. |
| 6,517,514 B1 | 2/2003 | Campbell |
| 6,527,787 B1 | 3/2003 | Fogarty et al. |
| 6,540,764 B1 | 4/2003 | Kieturakis et al. |
| 6,796,960 B2 | 9/2004 | Cioanta et al. |
| 7,300,448 B2 | 11/2007 | Criscuolo et al. |

(56) References Cited

U.S. PATENT DOCUMENTS

| | | |
|---|---|---|
| 7,691,089 B2 | 4/2010 | Gresham |
| 8,454,645 B2 | 6/2013 | Criscuolo et al. |
| 8,926,508 B2 | 1/2015 | Hotter |
| 2014/0012194 A1* | 1/2014 | Terwiske ............... A61M 39/22 |
| | | 604/99.04 |
| 2014/0121515 A1* | 5/2014 | Vitullo ................ A61M 39/223 |
| | | 604/99.04 |

FOREIGN PATENT DOCUMENTS

| | | |
|---|---|---|
| EP | 0880939 A1 | 12/1998 |
| WO | 9206638 A1 | 4/1992 |
| WO | 9218056 A1 | 10/1992 |
| WO | 9221293 A1 | 12/1992 |
| WO | 9221295 A1 | 12/1992 |
| WO | 9309722 A1 | 5/1993 |
| WO | 9721461 A1 | 6/1997 |
| WO | 9912602 A1 | 3/1999 |
| WO | 0126724 A2 | 4/2001 |
| WO | 02096307 A2 | 12/2002 |
| WO | 2004032756 A2 | 4/2004 |

\* cited by examiner

SURGICAL ACCESS DEVICE INCLUDING A UNIVERSAL FLUID FLOW VALVE

FIELD

The present disclosure relates generally to surgical access devices. In particular, the present disclosure relates to a surgical access device including a single valve for directing fluid flow through different fluid flow pathways of the surgical access device.

BACKGROUND

In minimally invasive surgical procedures, including endoscopic and laparoscopic surgeries, a surgical access device permits the introduction of a variety of surgical instruments into a body cavity or opening. A surgical access device (e.g., a cannula or an access port) is introduced through an opening in tissue (e.g., a naturally occurring orifice or an incision) to provide access to an underlying surgical site in the body. The opening is typically made using an obturator having a blunt or sharp tip that may be inserted through a passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall, and is then removed to permit introduction of surgical instruments through the surgical access device to perform the surgical procedure.

Minimally invasive surgical procedures, including both endoscopic and laparoscopic procedures, permit surgery to be performed on organs, tissues, and vessels far removed from an opening within the tissue. In laparoscopic procedures, the abdominal cavity is insufflated with an insufflation gas, e.g., $CO_2$, to create a pneumoperitoneum thereby providing access to the underlying organs. A laparoscopic instrument is introduced through the surgical access device into the abdominal cavity to perform one or more surgical tasks. The surgical access device may incorporate a seal to establish a substantially fluid tight seal about the laparoscopic instrument to preserve the integrity of the pneumoperitoneum. The surgical access device, which is subjected to the pressurized environment, e.g., the pneumoperitoneum, may include an inflatable anchor to prevent the surgical access device from backing out of the opening in the abdominal wall, for example, during withdrawal of the laparoscopic instrument therefrom. Typically, the surgical access device includes separate valves for insufflating the abdominal cavity and for inflating/deflating the inflatable anchor.

SUMMARY

This disclosure generally relates to a surgical access device including a universal fluid flow valve for selectively inflating or deflating an expandable anchor of the surgical access device and insufflating a working cavity (e.g., a body cavity) within a patient. The fluid flow valve is movable relative to a port having a plurality of fluid flow channels defined therein to allow a user (e.g., a surgeon) to open and close the fluid flow valve and to select one of the fluid flow channels for inflating (or deflating) the expandable anchor or insufflating the working cavity when the fluid flow valve is open. By incorporating a single valve into the surgical access device that can be utilized to open, close, and direct fluid flow through the surgical access device, instead of using separate valves for each fluid flow pathway, the number of components and assembly steps required to form and use the surgical access device is reduced, as well as the assembly time and/or material costs associated with the surgical access device, thereby simplifying the manufacture and set-up of the surgical access device and reducing cost to the manufacturer and/or user. Additionally, the universal fluid flow valve may be connected to a single fluid source, as compared to surgical access devices having separate valves, saving time and simplifying use to the user.

In an aspect, the disclosure provides a surgical access device including a cannula, an instrument housing coupled to the cannula, a port coupled to the instrument housing, and a valve disposed within the port. The cannula includes an elongated shaft defining an access lumen and an inflation lumen therethrough. The port includes an inflation channel and an insufflation channel defined therethrough. The inflation channel is in fluid communication with the inflation lumen of the cannula and the insufflation channel is in fluid communication with the access lumen of the cannula. The valve is movable within the port between an inflation position in which a passageway defined through the valve is aligned with the inflation channel of the port and an insufflation position in which the passageway of the valve is aligned with the insufflation channel of the port.

The valve may be slidable within the port between the inflation position and the insufflation position. The valve may be rotatable within the port between an open state in which the valve is in the inflation or the insufflation position and a closed state in which the passageway of the valve is out of alignment with the inflation and insufflation channels of the port.

The cannula may include an expandable anchor supported on the elongated shaft and in fluid communication with the inflation lumen. The expandable anchor may be a balloon.

The port may include a fluid connector portion configured for attachment to a fluid source and defining a first chamber therein. The inflation and insufflation channels of the port may be defined in a fluid channel housing portion of the port. The valve may be disposed between the fluid connector portion and the fluid channel housing portion of the port such that when the valve is in the inflation position, the passageway of the valve fluidly couples the first chamber of the fluid connector portion with the inflation channel of the fluid channel housing portion, and when the valve is in the insufflation position, the passageway of the valve fluidly couples the first chamber of the fluid connector portion with the insufflation channel of the fluid channel housing portion.

The valve may include a body portion extending along a longitudinal axis and the passageway may extend through the body portion along a transverse axis that is orthogonal to the longitudinal axis. The valve may include a pair of legs extending longitudinally from the body portion and flanges extending radially outwardly from the pair of legs. The body portion and the pair of legs of the valve may be disposed within a second chamber defined within a valve connector portion of the port. The valve may be slidable within the port such that when the valve is in the inflation position, the flanges of the valve contact a rim defined in the second chamber of the port and, when the valve is in the insufflation position, the flanges of the valve are spaced inwardly of the rim.

The valve may include a cap disposed at a first end portion thereof. The cap may include a handle extending radially outwardly therefrom. The cap may extend outwardly of or outside of the port. The cap may be laterally spaced from the port when the valve is in the inflation position, and the cap may abut the port when the valve is in the insufflation position. The handle may be aligned with a longitudinal axis of the cannula when the valve is in the open state, and the handle may be out of alignment with the longitudinal axis of the cannula when the valve is in the closed state.

The port may include a collar extending around the elongated shaft of the cannula. The insufflation channel of the port may be in fluid communication with a cavity defined in the instrument housing and the cavity may be in fluid communication with the access lumen of the cannula.

The details of one or more aspects of the disclosure are set forth in the accompanying drawings and the description below. Other features, objects, and advantages of the aspects described in this disclosure will be apparent from the description and drawings, and from the claims.

BRIEF DESCRIPTION OF THE DRAWINGS

The accompanying drawings, which are incorporated in and constitute a part of this specification, illustrate aspects and features of the disclosure and, together with the detailed description below, serve to further explain the disclosure, in which.

DETAILED DESCRIPTION

Aspects of the disclosure are described hereinbelow with reference to the accompanying drawings; however, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Like reference numerals refer to similar or identical elements throughout the description of the figures. Throughout this description, the term "proximal" refers to a portion of a structure, or component thereof, that is closer to a user, and the term "distal" refers to a portion of the structure, or component thereof, that is farther from the user.

Surgical access assemblies with obturators, known as trocar assemblies, are employed during minimally invasive surgery, e.g., laparoscopic surgery, and provide for the sealed access of surgical instruments into an insufflated body cavity, such as the abdominal cavity. The surgical access assemblies of the present disclosure include an instrument housing mounted on a cannula. An obturator (not shown) is insertable through the instrument housing and the cannula. The obturator can have a blunt distal end, or a bladed or non-bladed penetrating distal end, and can be used to incise and/or separate tissue of the abdominal wall so that the surgical access assembly can be introduced into the abdomen. The handle of the obturator can engage or selectively lock into the instrument housing of the surgical access assembly.

In various aspects, a bladeless optical trocar obturator may be provided that permits separation of tissue planes in a surgical procedure and visualization of body tissue fibers as they are being separated, thereby permitting a controlled traversal across a body wall. In other aspects, the trocar obturator may be bladeless without being optical, e.g., without providing contemporaneous visualization thereof through the distal tip of the trocar obturator. The bladeless trocar obturator may be provided for the blunt dissection of the abdominal lining during a surgical procedure.

Trocar obturators suitable for use with the surgical access assembly of the present disclosure are known and include, for example, bladed, bladeless, blunt, optical, and non-optical. For a detailed description of the structure and function of exemplary trocar assemblies, including exemplar trocar obturators and exemplar cannulas, please refer to PCT Publication No. WO 2016/186905, the entire content of which is hereby incorporated by reference herein.

Figure 1:
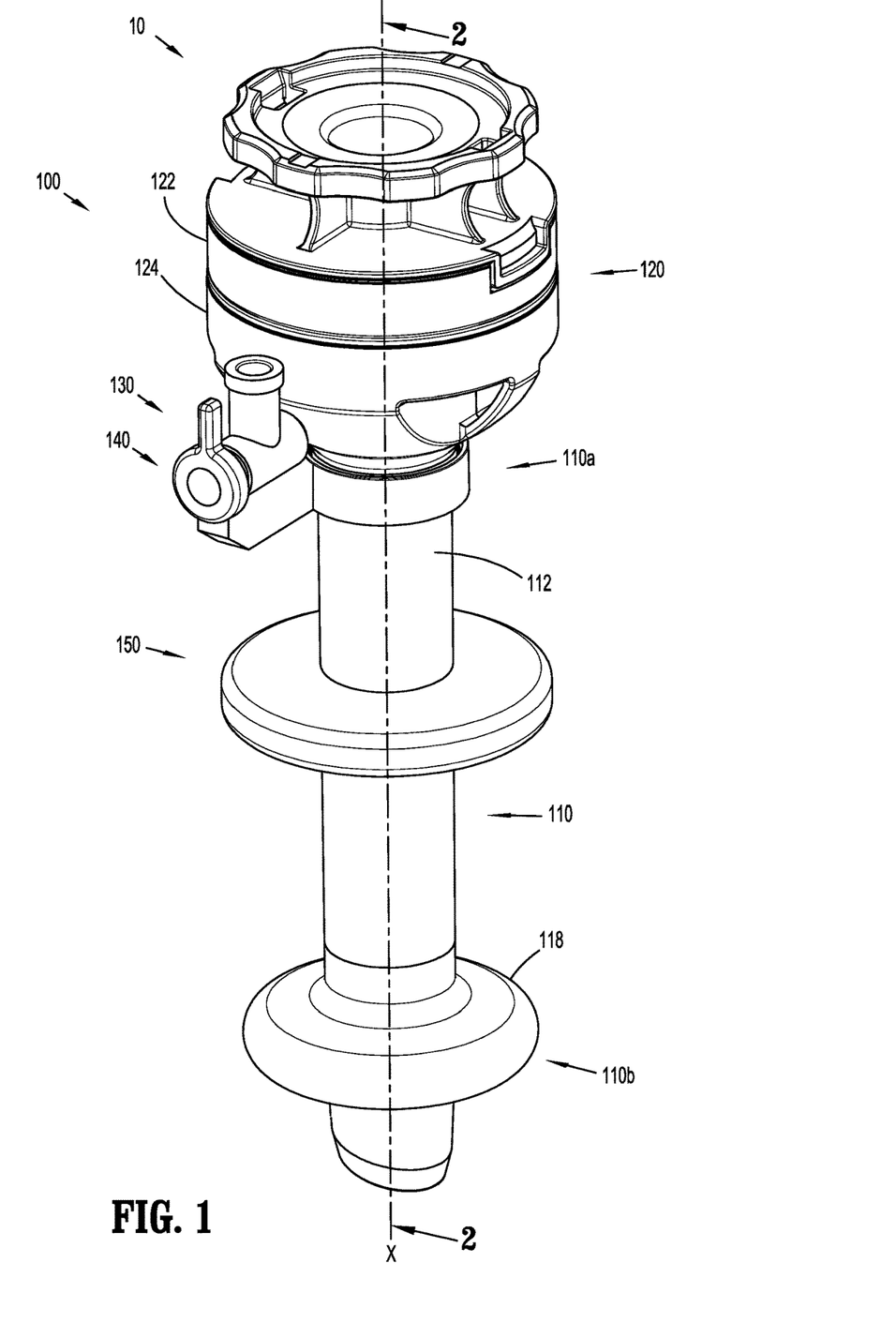
FIG. 1 is a perspective view of a surgical access assembly including a surgical access device and a retention collar in accordance with an aspect of the disclosure.
Figure 2:
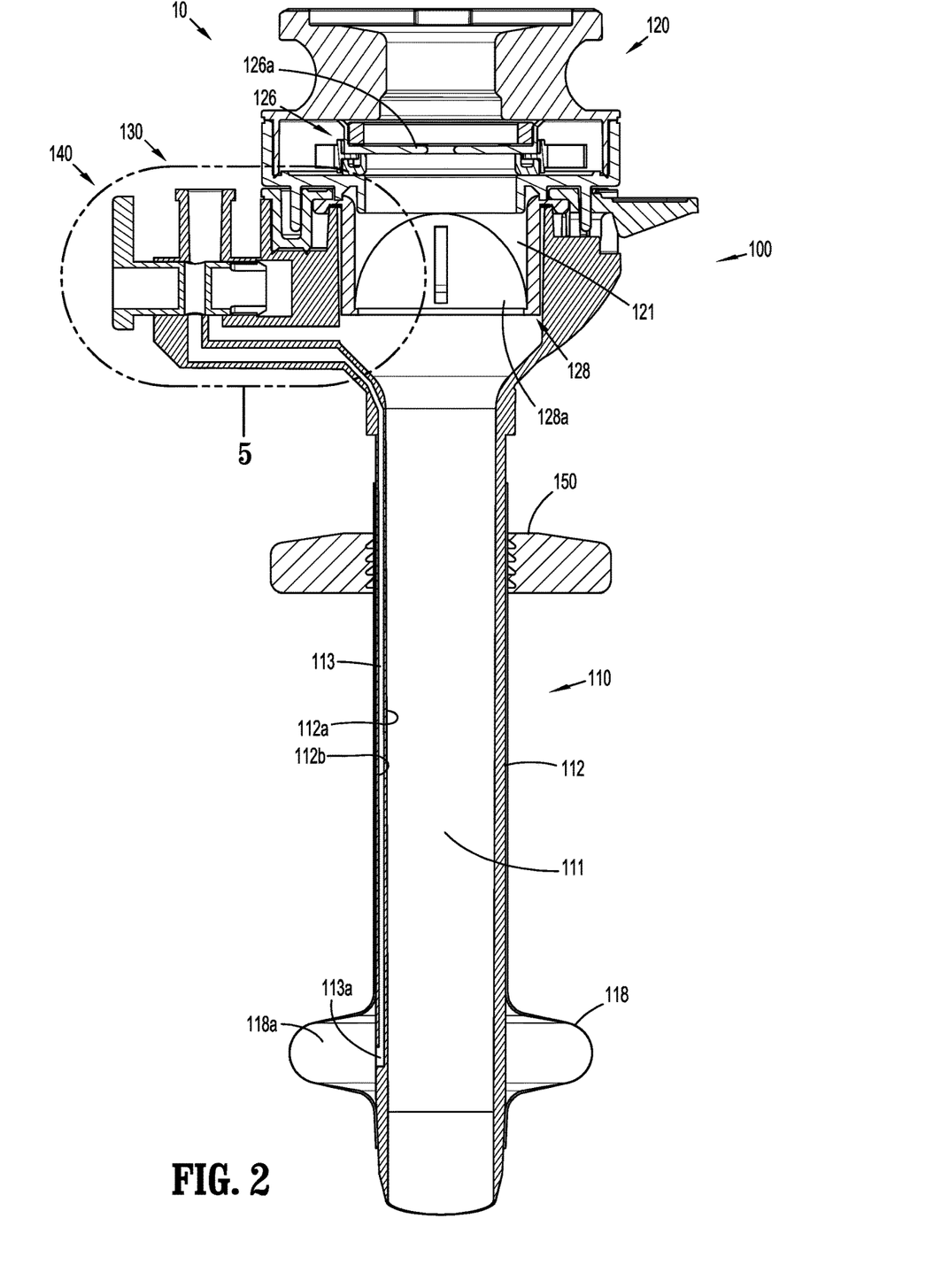
FIG. 2 is cross-sectional view of the surgical access assembly of FIG. 1, taken along section line 2-2 of FIG. 1.

FIGS. 1 and 2 illustrate a surgical access assembly 10 including a surgical access device 100 and a retention collar 150 supported on the surgical access device 100. The surgical access assembly 10 will further be described to the extent necessary to disclose aspects of the disclosure. For a detailed description of the structure and function of components of exemplary surgical access assemblies, surgical access devices, and/or retention collars, reference may be made to U.S. Pat. Nos. 7,300,448; 7,691,089; and 8,926,508, the entire content of each of which is hereby incorporated by reference herein.

The surgical access device 100 includes a cannula 110 and an instrument housing 120 secured to the cannula 110. The cannula 110 generally includes an elongated shaft 112 extending along a longitudinal axis "X." A proximal end portion 110a of the cannula 110 supports the instrument housing 120 thereon and a distal end portion 110b of the cannula 110 supports an expandable anchor 118 (e.g., an inflatable anchor, such as a balloon). The elongated shaft 112 includes an access lumen 111 defined by an inner surface 112a of the elongated shaft 112 that extends along the longitudinal axis "X" for reception and passage of a surgical instrument (not shown) therethrough.

The elongated shaft 112 also includes an inflation lumen 113 defined between the inner and outer surfaces 112a, 112b of the elongated shaft 112 that extends substantially parallel to the longitudinal axis "X." The inflation lumen 113 is open at a distal end 113a thereof through the outer surface 112b of the elongated shaft 112 such that the inflation lumen 113 is in fluid communication with an interior 118a of the expandable anchor 118. The expandable anchor 118 is movable from a collapsed position in which the expandable anchor 118 is positioned directly against the outer surface 112b of the elongated shaft 112 and an expanded position in which the expandable anchor 118 extends radially outwardly from the elongated shaft 112, as seen in FIG. 1. The expandable anchor 118 is movable through body tissue when in the collapsed position and secures the cannula 110 against an inner surface of tissue "T", such as an abdominal wall, when in the expanded position (see e.g., FIG. 9).

The retention collar 150 is supported on the elongated shaft 112 of the cannula 110. The retention collar 150 is releasably engageable with the elongated shaft 112, and slidable therealong to adjust the longitudinal position of the retention collar 150 on the elongated shaft 112. The retention collar 150 secures the cannula 110 against an outer surface of tissue "T" (see e.g., FIG. 9). The retention collar 150 may be formed from a compressible material to aid in sealing the opening into the tissue of the body wall. The retention collar 150 may include any known retention mechanism used on cannulas and/or trocars, such as foam collars.

The instrument housing 120 includes an upper housing section 122 and a lower housing section 124, and defines a cavity 121 therein that communicates with the access lumen 111 of the elongated shaft 112 of the cannula 110. The upper housing section 122 may be selectively attachable to, and detachable from, the lower housing section 124, and the lower housing section 124 may be releasably or permanently attached to the cannula 110. In aspects, either or both of the upper and lower housing sections 122, 124 of the instrument housing 120 may include knurls, indentations, tabs, or be otherwise configured to facilitate engagement by a user.

The instrument housing 120 supports a seal assembly 126 and a valve assembly 128 therein. The seal assembly 126 is disposed proximally of the valve assembly 128. The seal assembly 126 generally includes an instrument seal 126a for sealing around surgical instruments (not shown) inserted into the cannula 110, and the valve assembly 128 generally includes a zero-closure seal 128a for sealing the access lumen 111 of the cannula 110 in the absence of a surgical instrument inserted through the cannula 110. The seal assembly 126 and the valve assembly 128 prevent the escape of the insufflation fluid therefrom, while allowing surgical instruments to be inserted therethrough and into the body cavity. The instrument seal 126a may include any known instrument seal used in cannulas and/or trocars, such as septum seal. The zero-closure seal 128a may be any known zero-closure seal for closing off the passageway into the access lumen 111, such as a duckbill seal or flapper valve.

As shown in FIGS. 1-5, the surgical access device 100 includes a port 130 extending outwardly therefrom and includes a valve 140 disposed partially therein. The port 130 may be integrally formed as a single piece with the instrument housing 120 (e.g., the lower housing section 124) or the port 130 may be a separate component secured to the instrument housing 120. The port 130 may include a collar 132 extending around and engaged with the elongated shaft 112 of the cannula 110. The collar 132 may be secured to the cannula 110 by, for example, snap fit or friction fit engagement, although other mating structures and relationships are envisioned.

Figure 3:
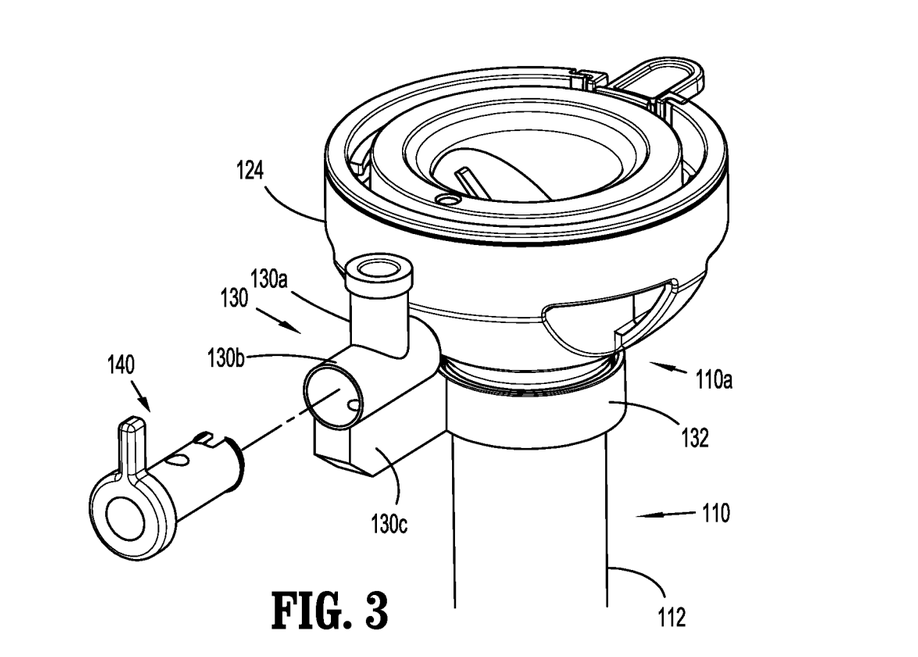
FIG. 3 is a perspective view of a proximal end portion of the surgical access device of FIG. 1, shown with an upper housing section of an instrument housing removed and a valve separated from a port of the surgical access device.
Figure 5:
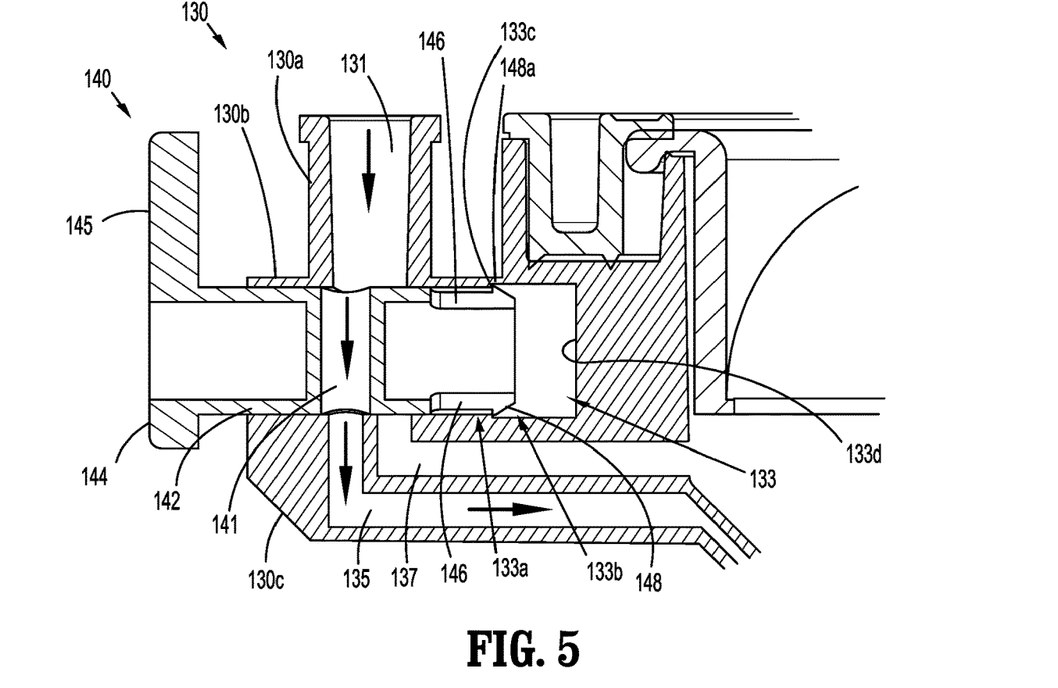
FIG. 5 is a close-up view of the area of detail indicated in FIG. 2, shown with the valve disposed in an open state and an inflation position.

As seen in FIGS. 3 and 5, the port 130 includes a fluid connector portion 130a, a valve connector portion 130b, and a fluid channel housing portion 130c. The fluid connector portion 130a is configured for attachment to a fluid source "F" (FIG. 9) and defines a first chamber 131 therein to allow for the flow of fluid (e.g., air, $CO_2$, or other gases or liquids) into and out of the port 130. The valve connector portion 130b defines a second chamber 133 therein that is configured to receive the valve 140 in a substantially fluid tight manner for controlling fluid flow from the fluid connector portion 130a to the fluid channel housing portion 130c. The fluid channel housing portion 130c contains separate inflation and insufflation channels 135, 137 defined therethrough that are in fluid communication with the inflation and access lumens 113, 111, respectively, of the cannula 110 (FIG. 2) for directing fluid flow to either the inflation lumen 113 or the access lumen 111. The port 130 allows fluid to flow from the fluid source and into the first chamber 131 of the fluid connector portion 130a which, in turn, is in selective communication with the inflation channel 135 or the insufflation channel 137 of the fluid channel housing portion 130c via the valve 140 positioned in the second chamber 133 of the valve connector portion 130b.

Figure 9:
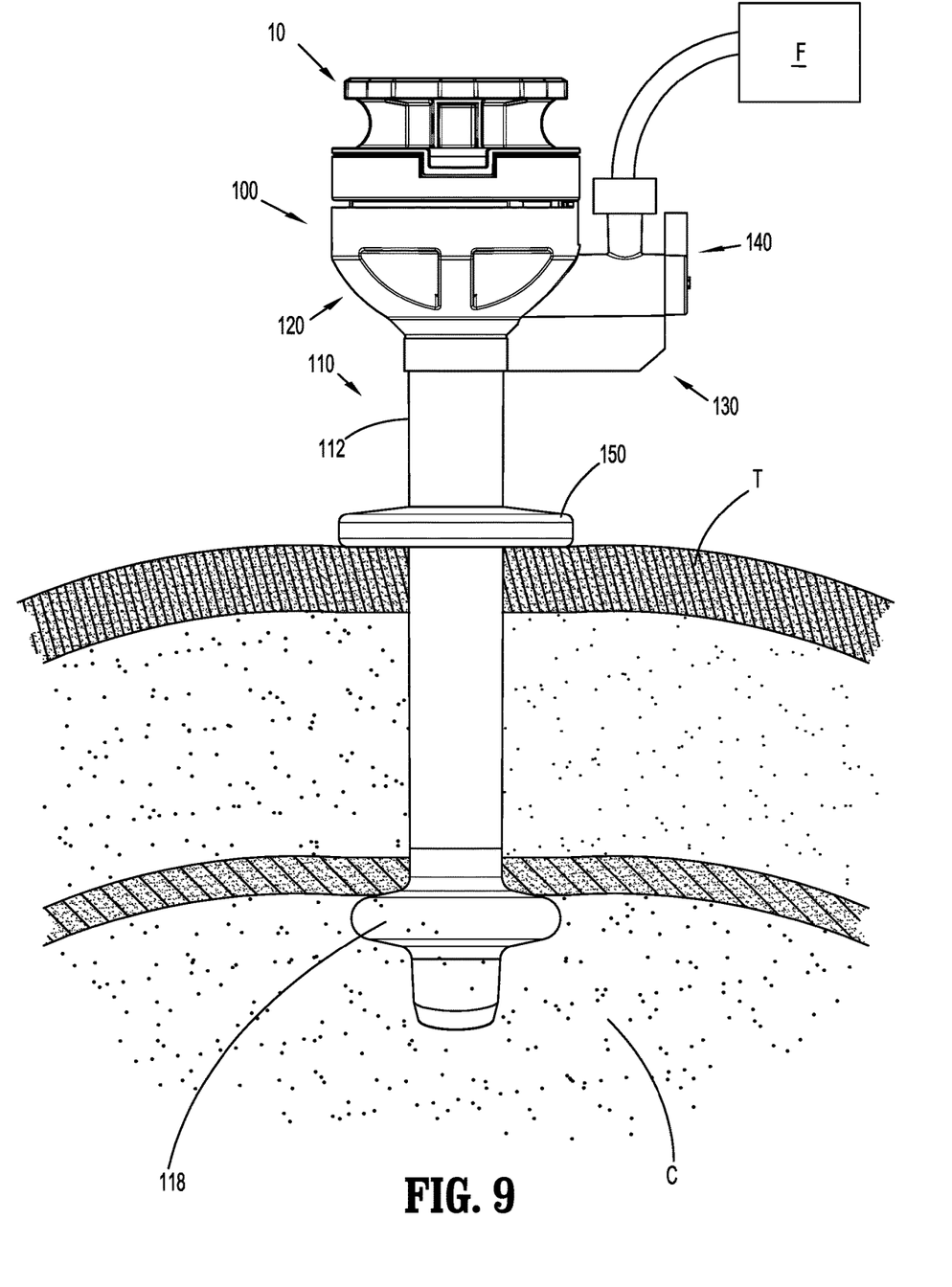
FIG. 9 is a side view of the surgical access assembly of FIG. 1, shown connected to a fluid source and positioned in tissue.

As seen in FIGS. 2 and 5, the inflation channel 135 of the port 130 is in fluid communication with the inflation lumen 113 of the cannula 110 to inflate or deflate the expandable anchor 118. The insufflation channel 137 of the port 130 is in fluid communication with the cavity 121 of the instrument housing 120 which, in turn, is in fluid communication with the access lumen 111 of the cannula 110 to insufflate a body cavity, such as an abdominal cavity (e.g., create a pneumoperitoneum). The insufflation channel 137 is disposed distally of the valve assembly 128 to maintain insufflation pressure within the body cavity. Accordingly, the inflation channel 135 and the inflation lumen 113 provide a fluid flow pathway from a fluid source "F" (FIG. 9) coupled to the port 130 to the expandable anchor 118, and the insufflation channel 137, the cavity 121, and the access lumen 111 provide a fluid flow pathway from the fluid source coupled to the port 130 to a body cavity "C" of a patient (FIG. 9).

Figure 4:
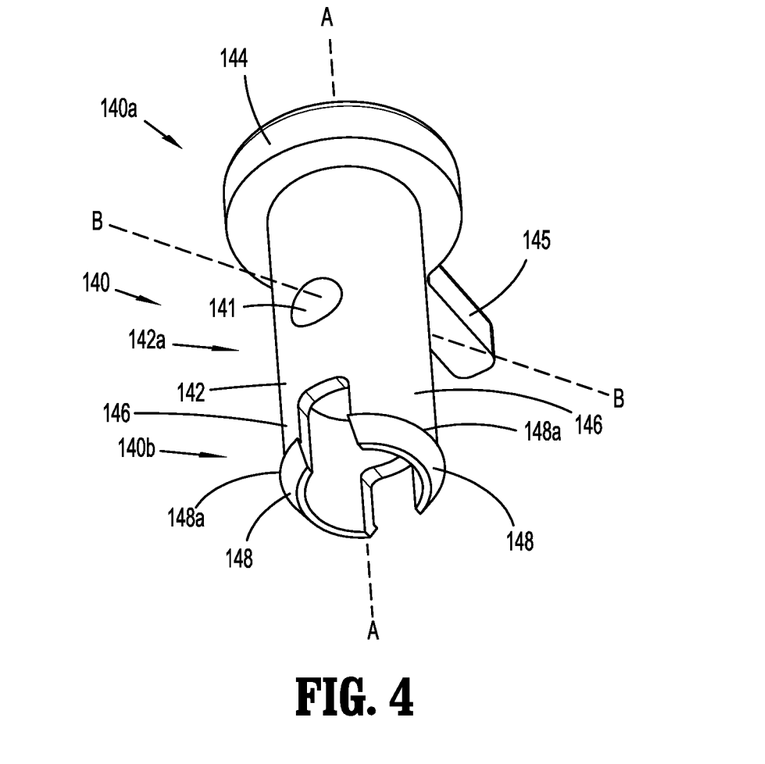
FIG. 4 is a perspective view of the valve of FIG. 3.

With continued reference to FIGS. 1-5, the valve 140 is coupled to the port 130. The valve 140 is slidable relative to the port 130 between an inflation position and an insufflation position, and is rotatable relative to the port between open and closed states, as described in further detail below. As seen in FIG. 4, the valve 140 includes a body portion 142 extending along a longitudinal axis "A" and having a generally cylindrical shape. A passageway 141 extends through a central portion 142a of the body portion 142 along a transverse axis "B" that is orthogonal to the longitudinal axis "A." A first end portion 140a of the valve 140 includes a cap 144 having a larger radial dimension than that of the body portion 142 and a handle 145 extending radially outwardly from the cap 144. A second end portion 140b of the valve 140 includes a pair of legs 146 extending longitudinally from the body portion 142 and a flange 148 extending radially outwardly from each leg 146. A lip 148a of each flange 148 faces the first end portion 140a of the valve 140.

As seen in FIG. 5, the body portion 142 and the pair of legs 146 of the valve 140 are positioned within the second chamber 133 of the port 130 such that the cap 144 extends outwardly of the port 130. The second chamber 133 is configured to slidably and rotatably receive the body portion 142 and the pair of legs 146 therein. The second chamber 133 includes an outer chamber portion 133a shaped and sized to retain the body portion 142 of the valve 140 therein in a fluid tight manner, and an inner chamber portion 133b having a larger dimension than the outer chamber portion 133a for accommodating the flanges 148 of the valve 140. A rim 133c is defined on a first end of the inner chamber portion 133b for catching the lip 148a of the flange 148 when the valve 140 is slid outwardly away from the port 130. This arrangement limits movement of the valve 140 and keeps the valve 140 coupled to the port 130 (e.g., a limit stop to prevent separation/expulsion). An end wall 133d is defined on a second end of the inner chamber portion 133b for limiting movement of the valve 140 when the valve 140 is slid inwardly into the port 130.

Figure 6:
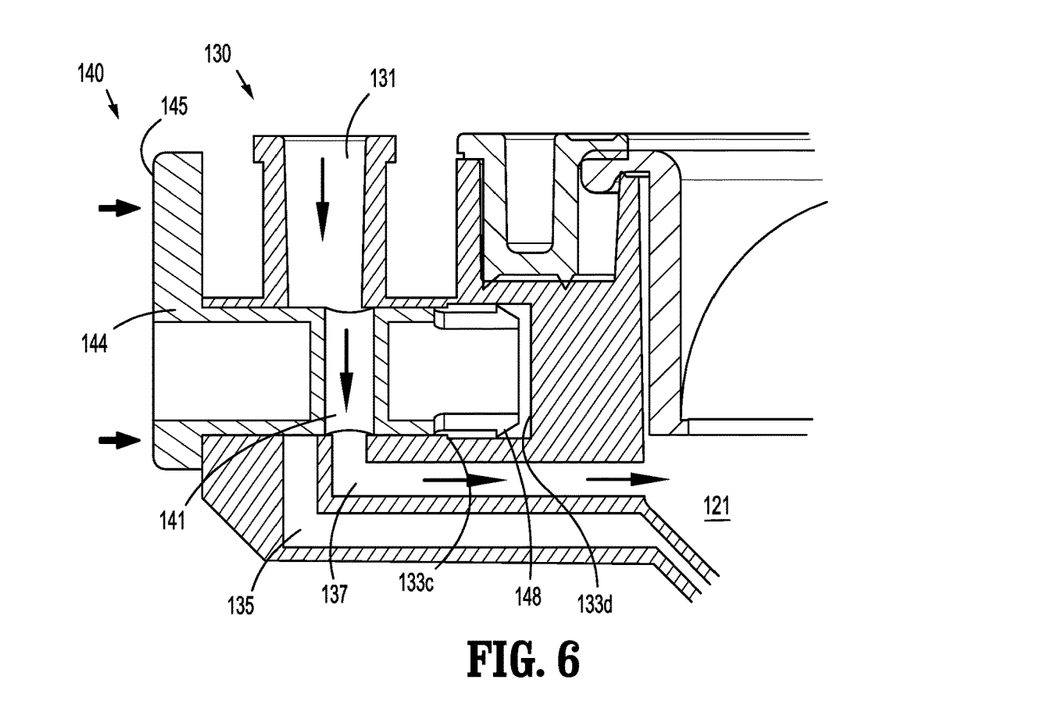
FIG. 6 is a close-up view of the surgical access device of FIG. 5, shown with the valve disposed in the open state and an insufflation position.

As shown in FIGS. 5 and 6, the valve 140 has an open state in which the passageway 141 defined therethrough is aligned with the first chamber 131 of the port 130 on one side thereof and with the inflation or insufflation channel 135, 137 on the other side thereof to provide a flow path through the port 130. In the open state, the handle 145 is aligned with the longitudinal axis "X" (FIG. 2) of the cannula 110 (e.g., the handle 145 extends along an axis parallel to the longitudinal axis "X" of the cannula 110). The valve 140 is laterally movable within the port 130 between an outward or inflation position, seen in FIG. 5, and an inward or insufflation position, seen in FIG. 6.

In the inflation position of FIG. 5, the flange 148 of the valve 140 is positioned against the rim 133c of the port 130, the cap 144 of the valve 140 is laterally spaced away from the port 130 (e.g., a gap is defined between the cap 144 and the port 130), and the passageway 141 defined through the valve 140 is aligned with the inflation channel 135 of the port 130 such that the passageway 141 fluidly couples the first chamber 131 of the port 130 with the inflation channel 135 to allow fluid to flow into or out of the inflation lumen 113 (FIG. 2) of the cannula 110 and thus, the expandable anchor 118. Accordingly, fluid is deliverable through a fluid flow pathway indicated by the arrows in FIG. 5 through the first chamber 131 of the port 130, the passageway 141 of the valve 140, the inflation channel 135 of the port 130, the inflation lumen 113 (FIG. 2) of the cannula 110, and into the expandable anchor 118 (FIG. 2) to expand the expandable anchor 118.

In the insufflation position of FIG. 6, the flange 148 of the valve 140 is laterally spaced inwardly of the rim 133c of the port 130 and may be adjacent to or abutting the end wall 133d of the port 130, the cap 144 of the valve 140 is disposed against the port 130 (e.g., no gap is present between the cap 144 and the port 130), and the passageway 141 defined through the valve 140 is aligned with the insufflation channel 137 of the port 130 such that the passageway 141 fluidly couples the first chamber 131 of the port 130 with the insufflation channel 137 to allow fluid to flow into or out of the access lumen 111 of the cannula 110 and thus, into or out of a body cavity within which the cannula 110 is placed. Accordingly, fluid is deliverable through a fluid flow pathway indicated by the arrows in FIG. 6 through the first chamber 131 of the port 130, the passageway 141 of the valve 140, the insufflation channel 137 of the port 130, the cavity 121 of the instrument housing 120, and into the access lumen 111 (FIG. 2) of the cannula 110 to insufflate the body cavity "C" (FIG. 9).

Figure 7:
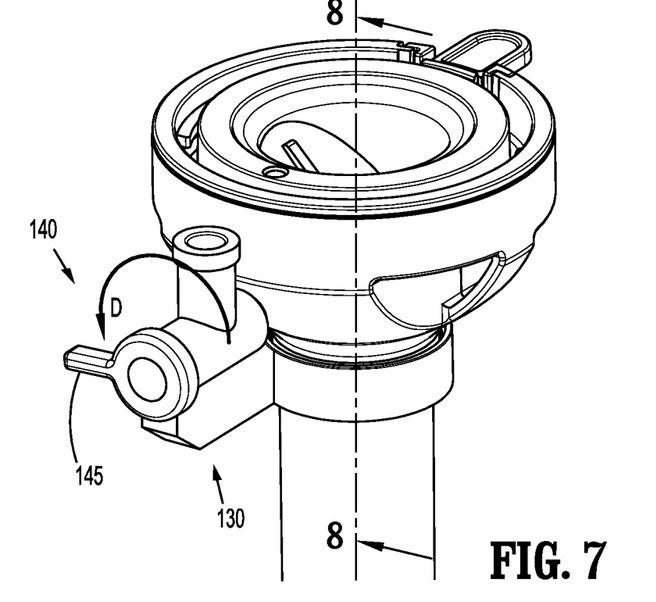
FIG. 7 is a perspective view of a proximal end portion of the surgical access device of FIG. 1, shown with the upper housing section of the instrument housing removed and the valve disposed in a closed state.
Figure 8:
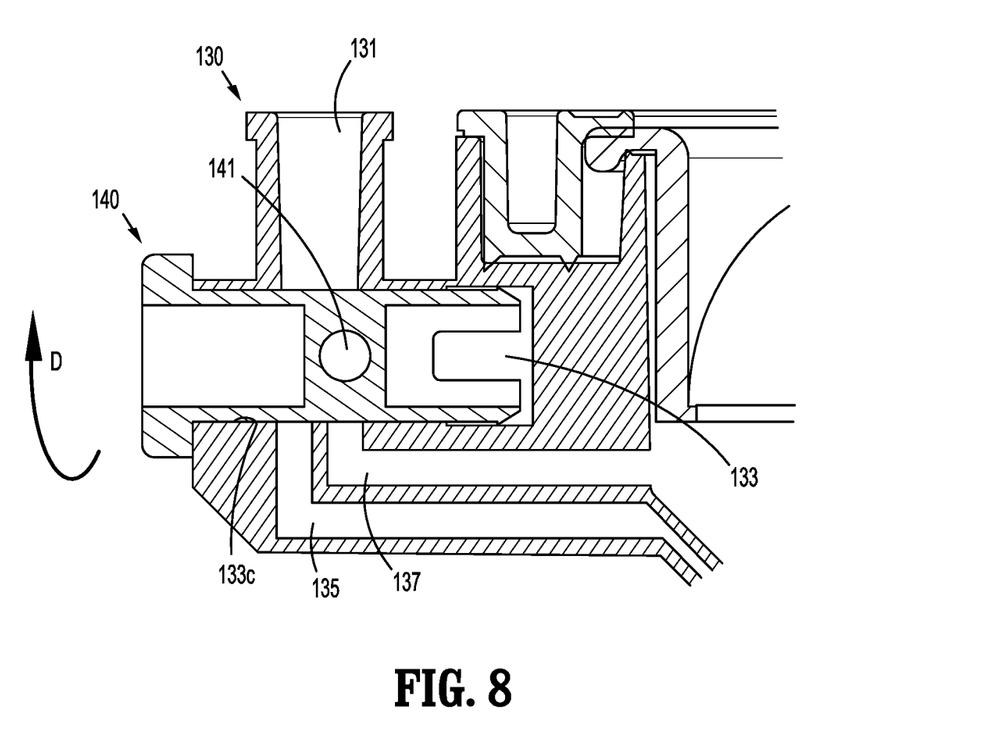
FIG. 8 is a cross-sectional view of the surgical access assembly of FIG. 7, taken along section line 8-8 of FIG. 7.

As shown in FIGS. 7 and 8, the valve 140 is movable to a closed state in which the passageway 141 defined therethrough is not aligned (e.g., out of alignment) with the first chamber 131 of the port 130 or either of the inflation or insufflation channels 135, 137. Rather, the valve 140 is rotated so that the passageway 141 of the valve 140 faces an inner wall 133e of the second chamber 133 of the port 130 effectively interrupting or disconnecting the fluid flow path through the port 130 and preventing the flow of fluid therethrough. The valve 140 is moved to the closed state by rotating the handle 145 of the valve 140 in the direction of arrow "D" so that the handle 145 is no longer aligned (e.g., out of alignment) with the longitudinal axis "X" (FIG. 1) of the cannula 110 (e.g., the handle 145 extends along an axis that is not parallel to the longitudinal axis "X" of the cannula 110). In aspects, the handle 145 extends along an axis that is perpendicular to the longitudinal axis "X" when in the valve 140 is in the closed state.

Accordingly, the valve 140 is rotatable between the open and closed states and the slidable between the inflation and insufflation positions. In aspects, indicia may be provided on the port 130 and/or the valve 140 to indicate the state and/or position of the valve 140 relative to the port 130.

In a method of use, as shown in FIG. 9, the surgical access assembly 10 is positioned through tissue "T", such as an abdominal wall. The elongated shaft 112 of the cannula 110 is received through the tissue "T" (e.g., by utilizing an obturator (not shown) to facilitate entry of the cannula 110 through the tissue), and the expandable anchor 118 is inflated within a body cavity "C" on a first side of the tissue "T" to prevent the cannula 110 from being withdrawn through the tissue "T". The expandable anchor 118 is inflated by connecting the port 130 of the surgical access device 100 to a fluid source "F" and moving the valve 140 to the open state and the inflation position seen in FIG. 5 thereby allowing pressurized fluid to be introduced from the fluid source "F" through the port 130 and the valve 140, the cannula 110, and into the expandable anchor 118 causing the expandable anchor 118 to expand.

The retention collar 150 is slid distally along the elongated shaft 112 of the cannula 110 until the retention collar 150 abuts or presses on a second side of the tissue "T" disposed outside of the body cavity "C". The tissue "T" is thus sandwiched between the expandable anchor 118 and the retention collar 150 to prevent the cannula 110 from being withdrawn from or over-inserted into the tissue "T". In this manner, the surgical access assembly 10 is secured to the tissue "T" and longitudinal movement of the cannula 110 relative to the tissue "T" is prevented or minimized throughout insertion, withdrawal, and/or manipulation of a surgical instrument (not shown) through the cannula 110.

The body cavity "C" is insufflated by moving the valve 140 to the open state and the insufflation position seen in FIG. 6 so that the fluid source "F" that is coupled to the port 130 pressurizes the body cavity by allows fluid from the fluid source "F" to be introduced through the port 130 and the valve 140, the instrument housing 120, the cannula 110, and into the body cavity "C" to create a working space therein.

Surgical instruments (not shown) may then be introduced through the surgical access assembly 10 and into the body cavity "C" to perform one or more surgical tasks. The surgical instruments may be, for example, laparoscopic or endoscopic clip appliers, graspers, dissectors, retractors, staplers, laser probes, photographic devices, tubes, endoscopes, laparoscopes, electro-surgical devices, etc. At any time during the surgical procedure, if the cannula 110 needs to be adjusted within the tissue "T" or insufflation of the body cavity "C" needs to be adjusted, the valve 140 of the surgical access device 100 may be moved to the appropriate state and/or position to allow for fluid flow through the appropriate fluid flow pathway, as needed or desired.

Following the surgical procedure, the expandable anchor 118 is deflated to permit the withdrawal of the surgical access assembly 10 from the tissue "T". The expandable anchor 118 is deflated by moving the valve 140 to the open state and the inflation position seen in FIG. 5 and either reversing the flow of fluid from the fluid source "F" or allowing the pressurized fluid within the expandable anchor 118 to escape through the fluid flow pathway causing the expandable anchor 118 to retract or collapse.

It should be understood that while aspects of the disclosure have been described, other aspects are possible.

For example, while the surgical access device is described as having inflation and insufflation fluid flow pathways, other configurations are additionally or alternatively possible. For example, the surgical access device may include additional or alternative fluid flow pathway(s) and the port of the surgical access device may be modified to accommodate fluid flow through the additional or alternative fluid flow pathway(s).

As another example, while the valve of the surgical access device is described as having an outward or inflation position and an inward or insufflation position, these positions may be switched depending upon the configuration of the inflation and insufflation channels within the port and the inflation and access lumens within the cannula.

While aspects of the disclosure have been described and shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be effected by one skilled in the art without departing from the scope or spirit of the disclosure. Additionally, the elements and features shown and described in connection with certain aspects of the disclosure may be combined with the elements and features of certain other aspects without departing from the scope of the present disclosure, and that such modifications and variation are also included within the scope of the present disclosure. Therefore, the above description should not be construed as limiting, but merely as exemplifications of aspects of the disclosure. Thus, the scope of the disclosure should be determined by the appended claims and their legal equivalents, rather than by the examples given.

What is claimed is:

1. A surgical access device comprising:
a cannula including an elongated shaft, the cannula including an access lumen and an inflation lumen extending through the elongated shaft;
an instrument housing coupled to the cannula;
a port coupled to the instrument housing, the port including an inflation channel and an insufflation channel defined through the port, the inflation channel in fluid communication with the inflation lumen of the cannula and the insufflation channel in fluid communication with the access lumen of the cannula; and
a valve disposed within the port, the valve including a passageway defined through the valve, the valve slidable axially within the port between an inflation position in which the passageway defined through the valve is aligned with the inflation channel of the port and an insufflation position in which the passageway of the valve is aligned with the insufflation channel of the port.

2. The surgical access device of claim 1, wherein the valve is rotatable within the port between an open state in which the valve is in the inflation position or the insufflation position and a closed state in which the passageway of the valve is out of alignment with the inflation channel and the insufflation channel of the port.

3. The surgical access device of claim 2, wherein the valve includes a cap disposed at a first end portion of the valve, the cap including a handle extending radially outwardly therefrom.

4. The surgical access device of claim 3, wherein, when the valve is in the inflation position, the cap is laterally spaced from the port, and when the valve is in the insufflation position, the cap abuts the port.

5. The surgical access device of claim 3, wherein, when the valve is in the open state, the handle is aligned with a longitudinal axis of the cannula, and when the valve is in the closed state, the handle is out of alignment with the longitudinal axis of the cannula.

6. The surgical access device of claim 1, wherein the cannula includes an expandable anchor supported on the elongated shaft and in fluid communication with the inflation lumen.

7. The surgical access device of claim 6, wherein the expandable anchor is a balloon.

8. The surgical access device of claim 1, wherein the port includes a fluid connector portion configured for attachment to a fluid source and defines a first chamber in the fluid connector portion.

9. The surgical access device of claim 8, wherein the inflation channel and the insufflation channel of the port are defined in a fluid channel housing portion of the port.

10. The surgical access device of claim 9, wherein the valve is disposed between the fluid connector portion and the fluid channel housing portion of the port such that when the valve is in the inflation position, the passageway of the valve fluidly couples the first chamber of the fluid connector portion with the inflation channel of the fluid channel housing portion, and when the valve is in the insufflation position, the passageway of the valve fluidly couples the first chamber of the fluid connector portion with the insufflation channel of the fluid channel housing portion.

11. The surgical access device of claim 1, wherein the valve includes a body portion extending along a longitudinal axis and the passageway extends through the body portion along a transverse axis that is orthogonal to the longitudinal axis.

12. The surgical access device of claim 11, wherein the valve includes a pair of legs extending longitudinally from the body portion and flanges extending radially outwardly from the pair of legs.

13. The surgical access device of claim 12, wherein the body portion and the pair of legs of the valve are disposed within a second chamber defined within a valve connector portion of the port.

14. The surgical access device of claim 13, wherein, when the valve is in the inflation position, the flanges of the valve contact a rim defined in the second chamber of the port and, when the valve is in the insufflation position, the flanges of the valve are spaced inwardly of the rim.

15. The surgical access device of claim 1, wherein the port includes a collar extending around the elongated shaft of the cannula.

16. The surgical access device of claim 1, wherein the insufflation channel of the port is in fluid communication with a cavity defined in the instrument housing and the cavity is in fluid communication with the access lumen of the cannula.

17. The surgical access device of claim 16, wherein the cavity of the instrument housing and the access lumen of the cannula are longitudinally aligned along a longitudinal axis.

18. The surgical access device of claim 16, wherein the instrument housing includes at least one of a seal assembly or a valve assembly disposed within the cavity of the instrument housing, and the insufflation channel of the port is in communication with the cavity distal to the at least one of the seal assembly or the valve assembly.

19. The surgical access device of claim 1, wherein the port extends outwardly from a side surface of the instrument housing.

20. The surgical access device of claim 1, wherein the access lumen is defined by an inner surface of the elongated shaft and extends along a central longitudinal axis of the elongated shaft, and the inflation lumen is defined between the inner surface of the elongated shaft and an outer surface of the elongated shaft, the inflation lumen extending along a longitudinal axis that is substantially parallel to the central longitudinal axis.

\* \* \* \* \*